(12) United States Patent
Wondrak et al.

(10) Patent No.: US 7,217,739 B2
(45) Date of Patent: May 15, 2007

(54) METHOD FOR INDUCING CELL DEATH WITH CARBONYL SCAVENGERS

(75) Inventors: Georg T. Wondrak, Tucson, AZ (US); Myron K. Jacobson, Tucson, AZ (US); Elaine L. Jacobson, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 148 days.

(21) Appl. No.: 11/069,292

(22) Filed: Mar. 1, 2005

(65) Prior Publication Data
US 2005/0197400 A1    Sep. 8, 2005

Related U.S. Application Data

(60) Provisional application No. 60/549,805, filed on Mar. 2, 2004.

(51) Int. Cl.
*A61K 31/13* (2006.01)
*A61K 31/195* (2006.01)

(52) U.S. Cl. .............. 514/665; 514/562; 514/13; 514/55; 514/54

(58) Field of Classification Search .............. 514/665, 514/562, 13, 55, 54
See application file for complete search history.

(56) References Cited

U.S. PATENT DOCUMENTS 5,668,117 A * 9/1997 Shapiro ............... 514/55
6,417,235 B2 * 7/2002 Jacobson et al. ........... 514/665
6,613,793 B2 * 9/2003 Burman et al. ............. 514/423
6,716,635 B2 * 4/2004 Jacobson et al. ............. 436/87
6,811,788 B2 * 11/2004 Yu .......................... 424/278.1
7,071,164 B2 * 7/2006 Quirk et al. ................ 514/13
2002/0197400 A1 * 12/2002 Kao et al. .................. 427/240
2003/0096757 A1 * 5/2003 Quirk et al. ................ 514/14

OTHER PUBLICATIONS

Daniel et al., "Organic copper complexes as a new class of proteasome inhibitors . . . ", Data base:Science Direct, Biochemical Pharmacology, vol. 67, Issue 6, Mar. 15, 2004(online available Dec. 29, 2003), pp. 1139-1151.*
Tsimberidou et al., Recombinant human soluble tumor necrosis factor(TNF) . . . , Database: Springer-Verlag 2002, Cancer Chemotherapy and Pharmacology, DOI 10.1007/d00282-002-0479-6, Jul. 26, 2002.*
Akhand et al., Glyoxal and Methylglyoxal trigger distinct signals . . . , Database:Elsevier, Free Radical Biology & Medicine, 2001, vol. 31, No. 1, pp. 20-30.*

* cited by examiner

*Primary Examiner*—Vickie Kim
(74) *Attorney, Agent, or Firm*—Fulbright & Jaworski LLP (57) ABSTRACT

Carbonyl scavengers, which have been recognized for their ability to react with reactive carbonyl species, have been implicated as agents that can accelerate or induce the death of abnormal cells without having a parallel effect on normal cells. As such, they are useful therapeutic agents in cases where the acceleration or induction of cell death is desirable, such as in cells where the normal apoptotic pathways have been disrupted and where hyperproliferative cell growth occurs.

10 Claims, 8 Drawing Sheets

METHOD FOR INDUCING CELL DEATH WITH CARBONYL SCAVENGERS

RELATED APPLICATION

This application is a continuation in part of application Ser. No. 60/549,805, filed Mar. 2, 2004, and incorporated by reference in its entirety.

FIELD OF THE INVENTION

This invention relates to methods for inducing cell death, via using carbonyl scavengers, such as dicarbonyl scavengers.

BACKGROUND AND PRIOR ART

The rising incidence of skin disorders, including non-melanoma disorders, as well as melanoma skin cancer, has been well documented, as has the continued lack of effective treatments of premalignant and malignant stages of skin cancer.

Diegpen, et al., *Br. J. Dermatology* 146: 1–6 (2002), have documented non-melanoma skin cancer, or "NMSC," as the most common type of cancer affecting Caucasian populations. Approximately 80% of NMSCs are basal cell carcinomas, and 20% are squamous cell carcinomas. The condition known as actinic keratosis is a precancerous condition, which may develop into squamous cell carcinoma. The rate of progression to the invasive, squamous cell carcinoma, is estimated to range to up to 20% per year. See May, *J. Am. Acad. Dermatol.* 42: 8–10 (2000).

While melanoma represents only about 5% of all skin cancers in the U.S., it accounts for nearly 80% of skin cancer deaths. Early diagnosis leads to a high rate of cure by surgical excision; however, malignant melanoma has a very high tendency for invasion and to metastasize. Melanoma cells are highly resistant toward chemotherapy, all forms of therapeutic induction of apoptosis, as well as to any form of therapy.

It has recently been observed that cellular carbonyl stress, mediated by endogenous, reactive carbonyl species, or "RCS," especially dicarbonyl compounds, including glyoxal, methylglyoxal, and malondialdehyde, which are formed during glycolysis and lipid peroxidation, are implicated in both proliferative signaling, and metastasis of human tumor cells. See, e.g., Taguchi, et al., *Nature* 405 (6784):354–60 (2000).

RCS—derived protein epitopes, referred to as "advanced glycation end products," or "AGEs," which are formed via reaction between RCS and tissue proteins, are found in abundance in melanoma, and AGEs are potent ligands of RAGE, which is a membrane receptor involved in melanoma proliferation and metastasis. See, e.g., Abe et al., *J. Invest. Dermatol.* 122(2), 461–467 (2004).

There is accumulating evidence to support the view that RCS which originate constitutively from increased tumor cells glycolysis, and mitochondrial lipid peroxidation, are small molecular anti-apoptotic modulators which suppress mitochondrial permeability transition pore opening, via covalent modifications. See, e.g., Speer, et al., *J. Biol. Chem.* 278(37), 34757–63.

Wondrak, et al., *Biochem. Pharmacol.* 7105: 1–13 (2002), have identified a series of very effective, non-toxic carbonyl scavengers, as being useful in therapeutic intervention of cellular carbonyl stress. This reference is incorporated by reference, as are U.S. Pat. No. 6,716,635, issued Apr. 6, 2004 and U.S. Pat. No. 6,417,235, issued Jul. 9, 2002. The '635 patent in particular gives a detailed explanation of RCS and RAGE compounds, mechanisms of action, how they are formed, and so forth.

It has now been found that these carbonyl scavengers have pronounced, apoptosis inducing impact on melanoma and other cancer cells, but not normal cells. This is a feature of the invention, as is set out in the examples which follow.

DETAILED DESCRIPTION OF PREFERRED EMBODIMENTS

EXAMPLE 1

This example delineates experiments which showed that 3-mercapto-D-valine ("D-penicillamine") induced apoptosis of malignant cell lines.

The murine melanoma cell line B16 was used, as were three human melanoma lines, i.e., G-361, A-375, and LOX. Samples of the cells were exposed to 10 mM of D-penicillamine continuously, over a 24 hour period. Apoptosis was measured using a standard assay, i.e., flow cytometric staining using annexin V-FITC/propidium iodide. As a control, normal human skin fibroblasts, i.e., "CF3" cells, were used.

Figure 1:
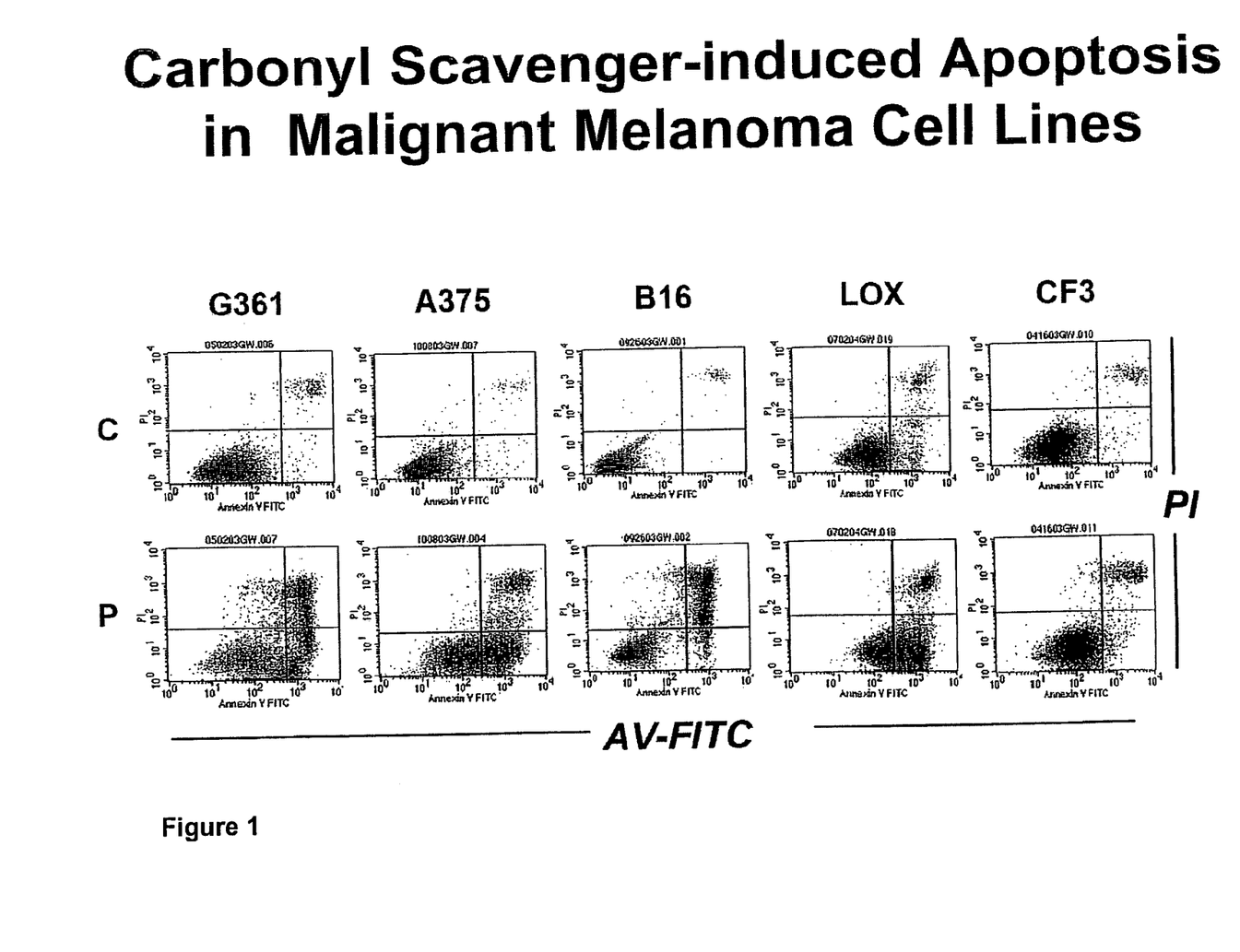
FIG. 1 depicts a comparison of induced apoptosis using D-penicillamine on malignant melanoma cell lines, of murine (B16) and human (G-361, A-375, LOX) cell lines. In this figure, "C" refers to a control while "P" refers to treatment with D-penicillamine.

The results, presented in FIG. 1, show control runs (no compound), and test runs (with compound), on the top and bottom, respectively. It is clear from these figures that apoptosis was induced in the malignant cells, while there was no change in the normal, CF3 cells.

In experiments not depicted in the figures, 3-mercaptoisoleucine yielded similar results.

EXAMPLE 2

In these experiments, D-penicillamine was added, at a concentration of 12.5 mM, to premalignant, immortalized human keratinocytes, or "HaCaT" cells, and the exposure was Continuous over 24 hours.

Figure 2:
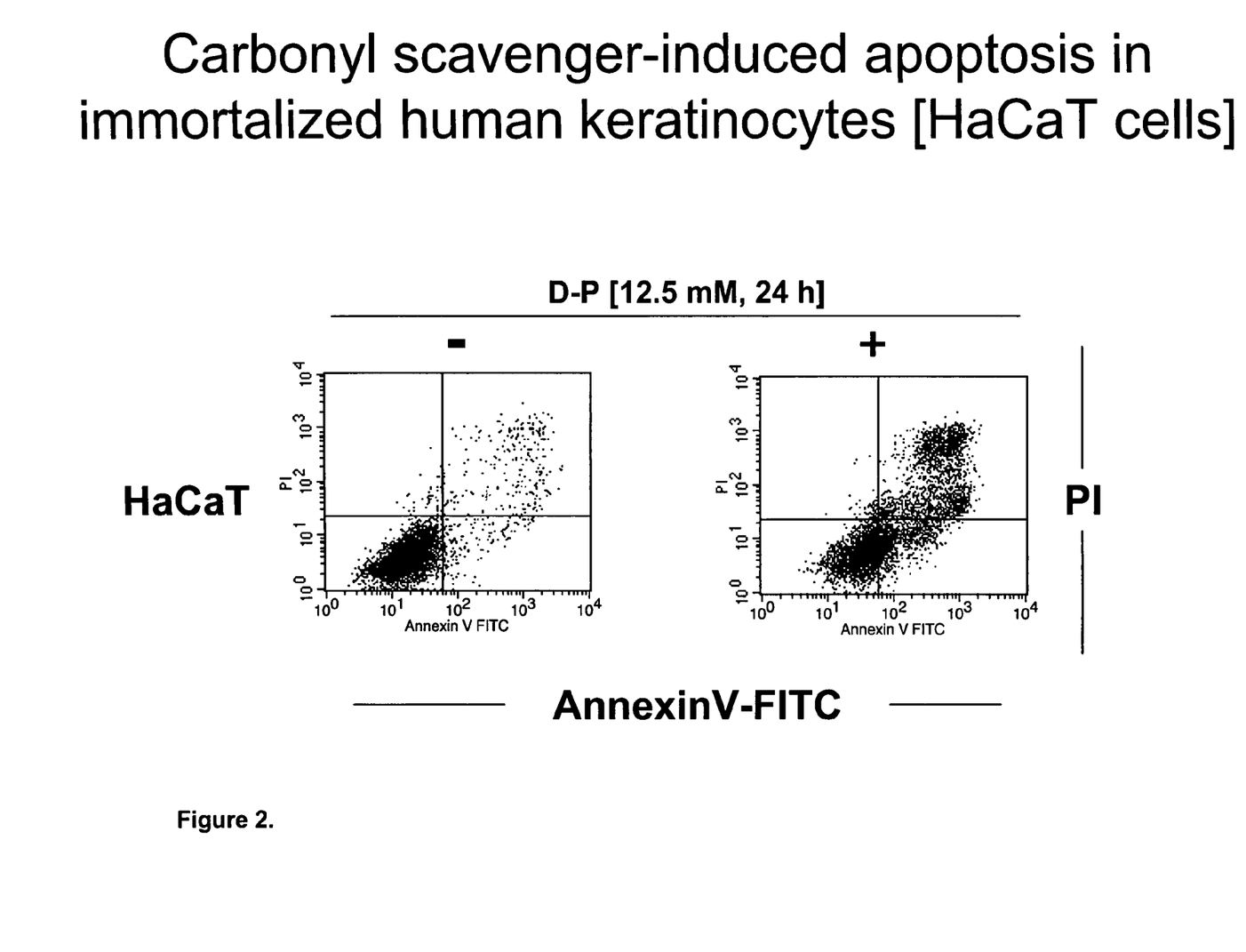
FIG. 2 summarizes the results of experiments on premalignant, immortalized human keratinocytes, following exposure to D-penicillamine.

In FIG. 2, the control (no compound) is on the left and test compound D-penicillaminie's effect is shown on the right. Again, apoptosis is indicated.

EXAMPLE 3

This set of experiments utilized both D-penicillamine, and its more lipophilic derivative, D-penicillamine methyl ester.

To make the derivative, 18 ml of $SOCl_2$ in 75 ml of MeOH which had been stored at $-10°$ C. was stirred, and varying amounts of D-penicillamine (15 g, 100.5 mmol) were added. Stirring continued while the mixture reached room temperature. The mixture was refluxed for 60 hours, and solvent was then evaporated, leaving a crude product (15.2 g, 93.3 mmol), which was dissolved in methanol, then crystallized with addition of ether. Crystallized product was collected, and dried under a vacuum, leaving 7.6 g of pure product. Its structure was confirmed by 'H-NMR and mass spectrometry. The m/z calculated for $C_6H_{14}O_2NS$ was 164.1 $[M+H]^+$, observed 164.1.

In each case, 10 mM of the test compound was used, over 24 hours, on human A431 cells, and apoptosis was measured as described, supra.

Figure 3:
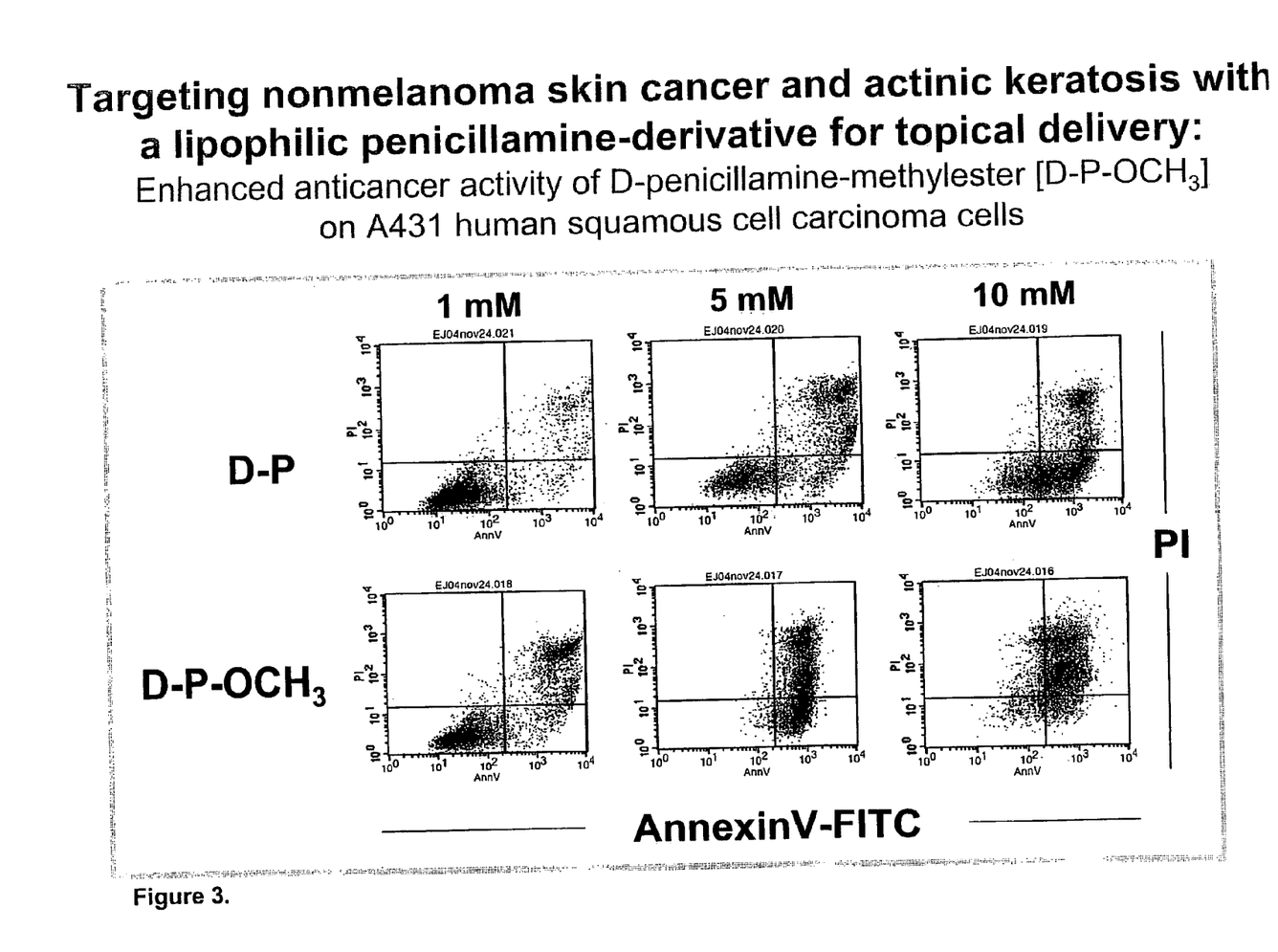
FIG. 3 shows the induction of apoptosis in malignant, human squamous cell carcinoma line A431, following exposure to D-penicillamine, as well as to D-penicillamine methyl ester.

In FIG. 3, "D-P" refers to D-penicillamine, while "D-P—$OCH_3$" is the methyl ester. A stronger apoptotic effect was seen with the ester.

EXAMPLE 4

The efficacy of the compounds on other cancers, epithelial cancers in particular, was determined. Human HeLa cervical adenocarcinoma cells were used, and tested with D-penicillamine, at 10 mM, and aminoguanidine, at 25 mM. These were tested with N-acetyl-D-penicillamine, which does not function as a carbonyl scavenger.

Figure 4:
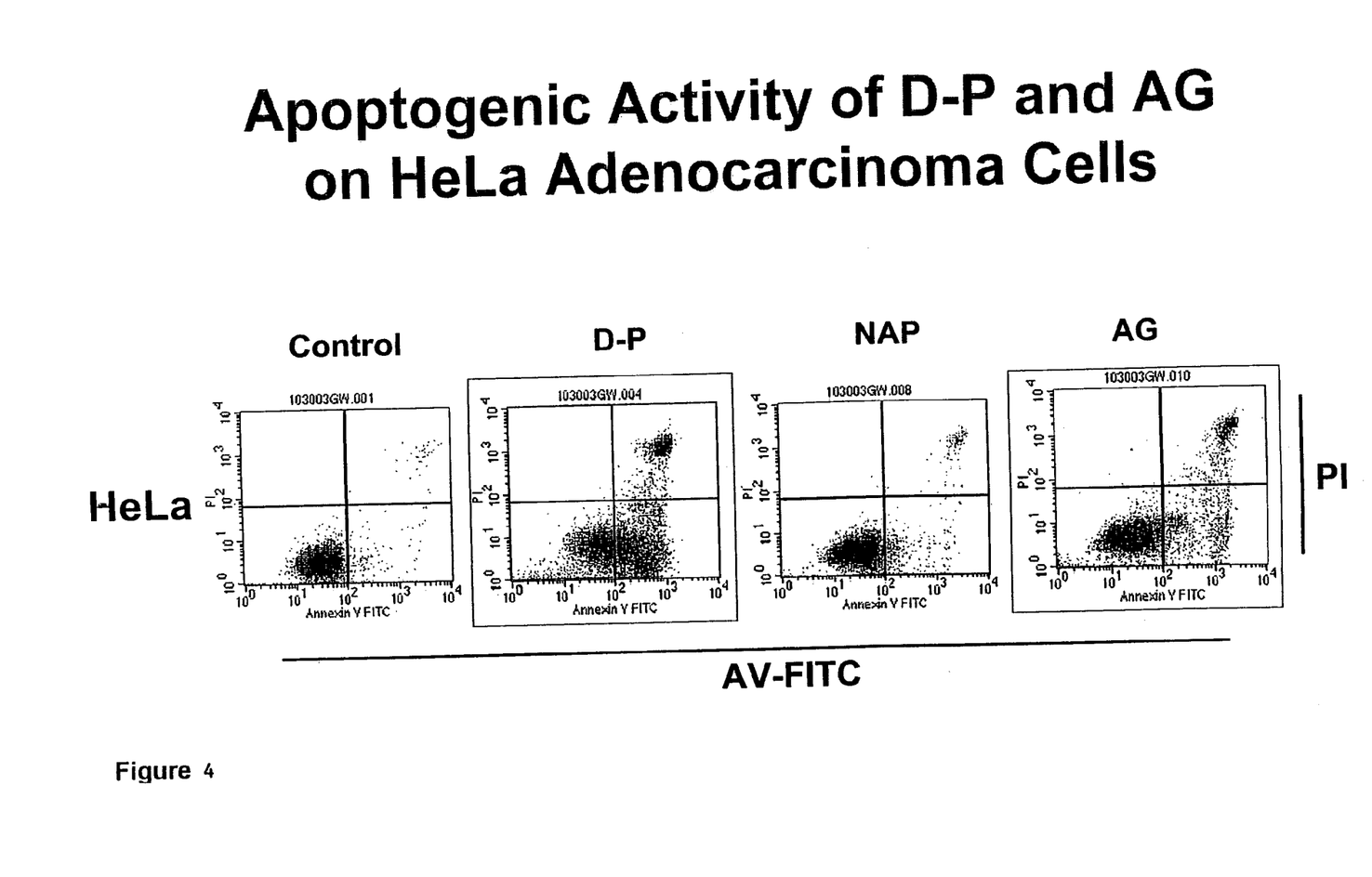
FIG. 4 presents a summary of results using D-penicillamine, N-acetyl-D-penicillamine and aminoguanidine on epithelial carcinoma cell lines.

FIG. 4 presents the results of these experiments with the control ("C"), D-penicillamaine ("D-P"), N-acetyl-D-Penicillamine ("NAP") and aminoguanidine ("AG"). Both D-penicillamine and aminoguanidine, known as carbonyl scavengers, were apoptosis inducers, while NAP was not.

EXAMPLE 5

3-methyl-3-ethyl-L-cysteine (3-mercaptoisoleucine, or "MEC") is a more lipophilic carbonyl scavenger than those tested previously. As increased lipophilicity can be desirable in topical delivery systems, it was of interest to test this compound.

MEC was synthesized, to 95% purity, in accordance with Leach, B. E. et al. "Synthesis of D, L-penicillamine from N-acetyl-D, L-penicillamine" in Clarke, H. T. ed., *The Chemistry of Penicillin*, (Princeton University Press, 1949), Pg. 466, and its structure was confirmed by 'H-NMR.

Malignant human melanoma cells A375, and normal fibroblasts (CF3), were tested, using 10 mM of MEC, with 24 hours of exposure.

Figure 5:
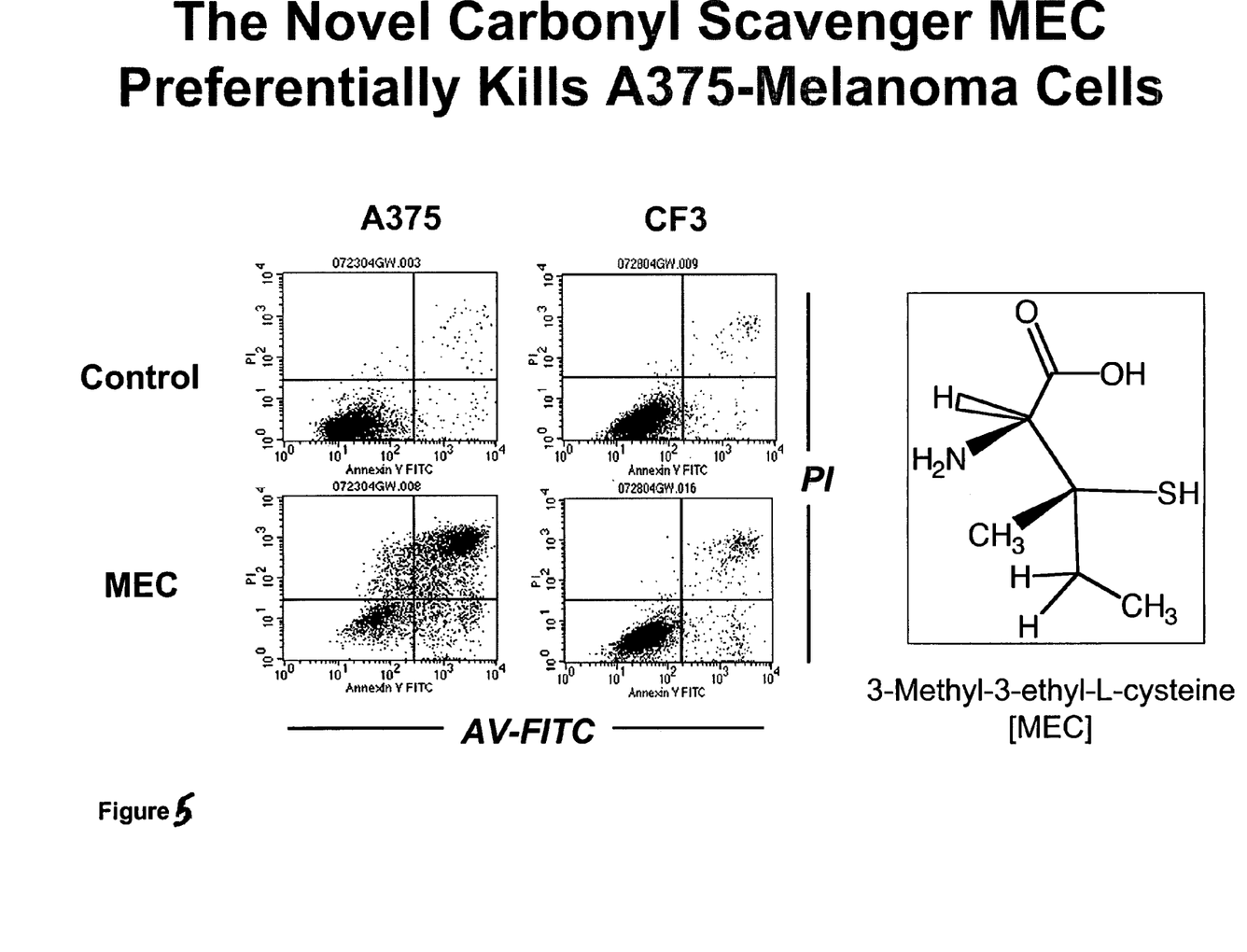
FIG. 5 compares induced apoptosis in human melanoma line A375 and normal fibroblast cell line CF3. The compound used was the lipophilic derivative of D-penicillamine, 3-mercaptoleucine.

Pronounced induction of apoptosis was seen in the malignant cells, but none was observed in the normal cells, as is seen in FIG. 5.

EXAMPLE 6

These experiments were designed to determine if there was a structure/function relationship. In other words, it was of interest to determine if activity as a carbonyl scavenger, but not as antioxidant, was important for anticancer activity.

The compound D-penicillamine (D-P), aminoguanidine (AG), N-acetyl-D-penicillamine (NAP), N-acetyl-L-cysteine (NAC), and penicillamine disulfide (PSS) were tested. D-P, NAC and NAP are known as antioxidants. D-P and aminoguanidine are known as carbonyl scavengers.

Figure 6:
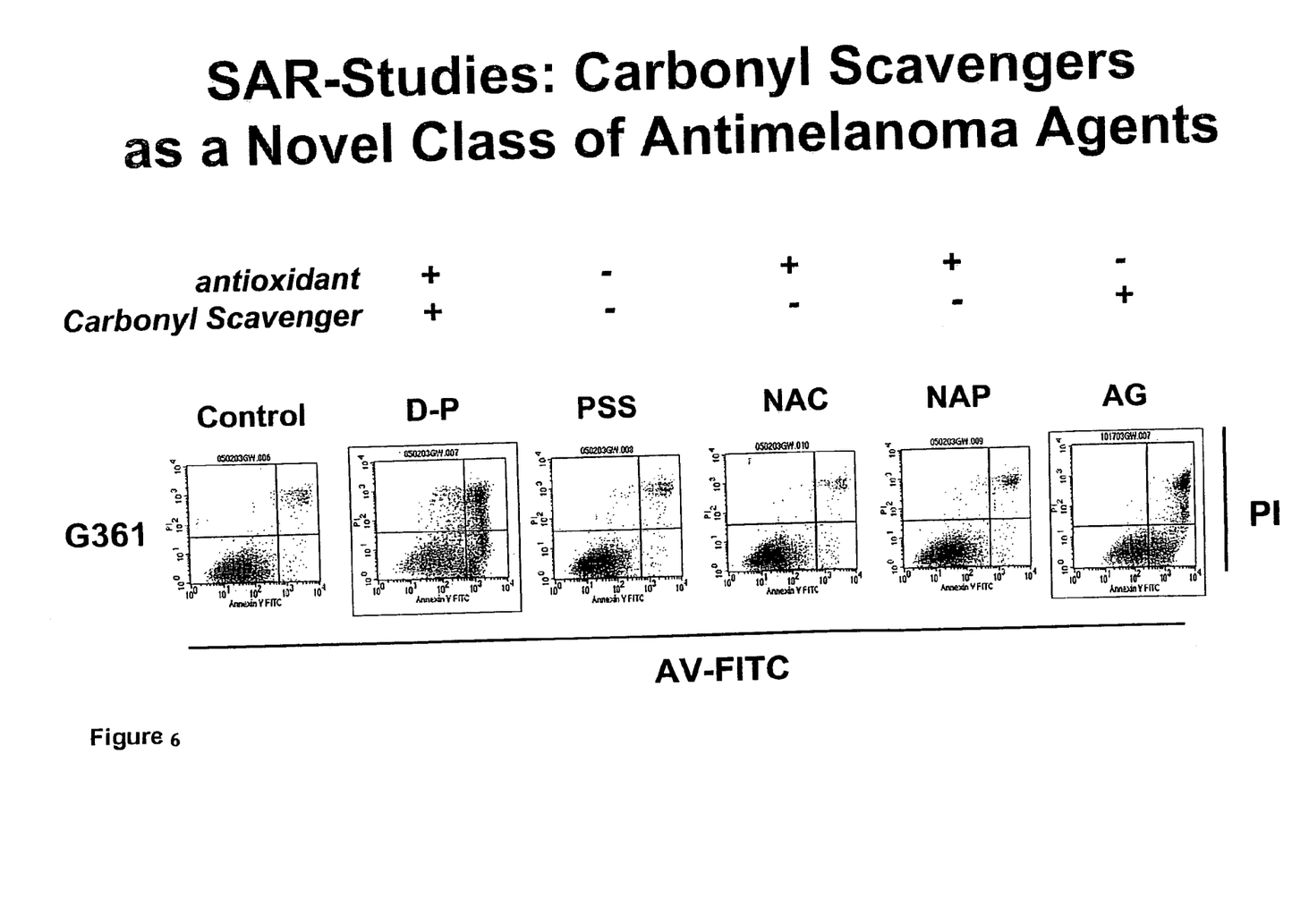
FIG. 6 shows that a structural requirement exists for carbonyl scavenger activity, where D-penicillamine, aminoguanidine, N-acetyl-D-penicillamine, and penicillamine disulfide were tested.

In tests on human melanoma cell line G-361, only D-P and AG induced apoptosis. These results suggest that there is a structural requirement for primary amino and thiol substituents, and that antioxidant activity does not correlate with apoptogenicity. FIG. 6 summarizes these results.

EXAMPLE 7

The therapeutic potential of carbonyl scavengers in treating cancer was shown in these experiments.

Figure 7:
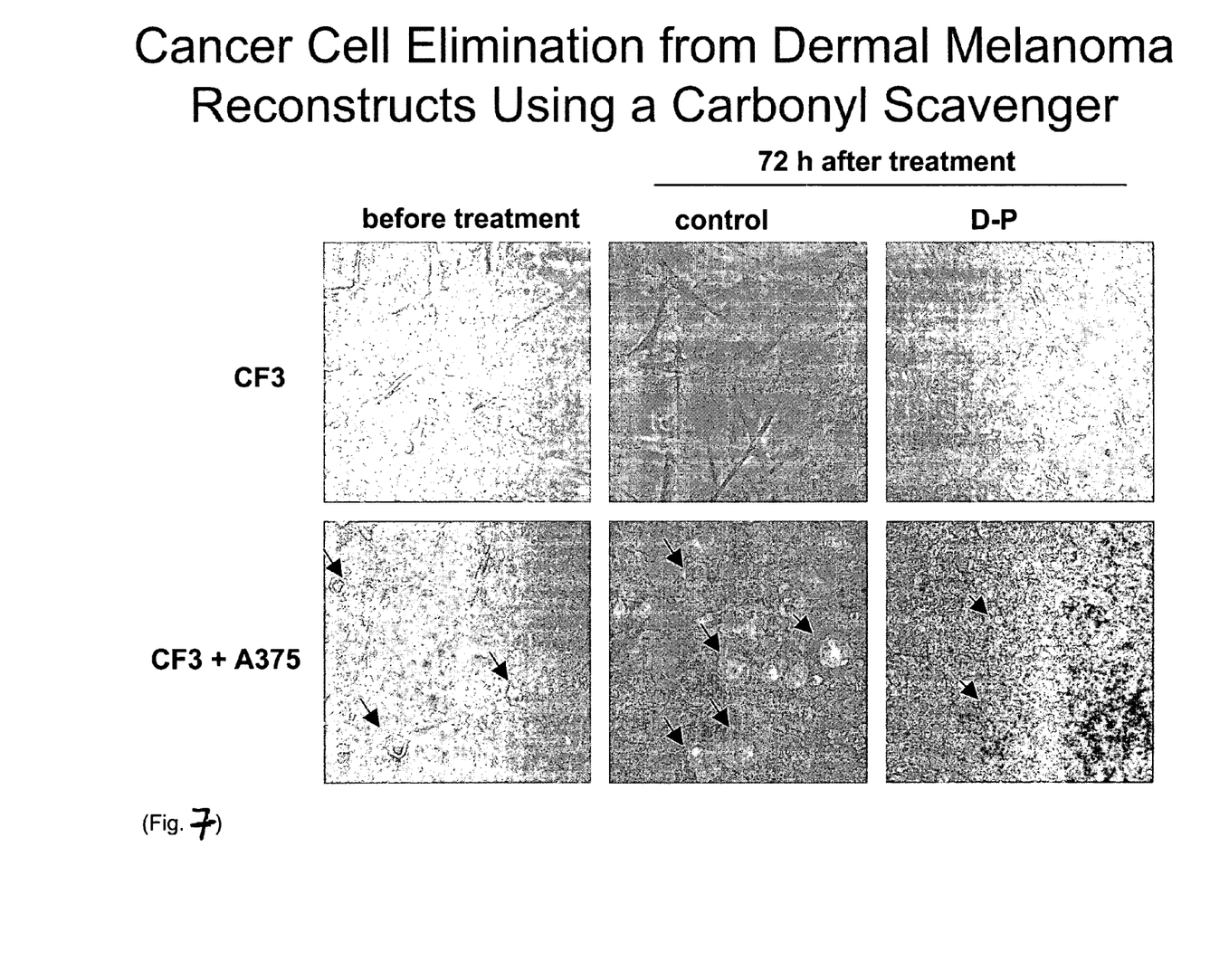
FIG. 7 shows the efficacy of compounds in accordance with the invention, in selectively eliminating malignant melanoma cells from a mix of normal and malignant cells.

A dermal melanoma reconstruct was made, where both CF3 fibroblast and A375 melanoma cells were embedded in a collagen matrix. Seventy two hours after "seeding" in the matrix, the melanoma cells have proliferated extensively, as the controls show, in FIG. 7. Treatment with 12.5 mM of D-P, however, eliminated the melanoma cells and maintained the structure integrity of the fibroblast collagen network.

EXAMPLE 8

These experiments show that the preferential apoptosis that the carbonyl scavenger treatment induced occurred with depolarization of mitochondrial transmembrane potential "$\Delta\Psi m$." The potentiometric dye JC-1 was used, following Reers, et al., *Biochemistry* 30 (18): 4480–6 (1991). The dye was administered 24 hours after 10 mM of D-penicillamine was added to medium. RCS pretreatment involved the use of 5 mM of phenylglyoxal, for 15 minutes, followed by washing with PBS and addition of fresh medium.

Figure 8:
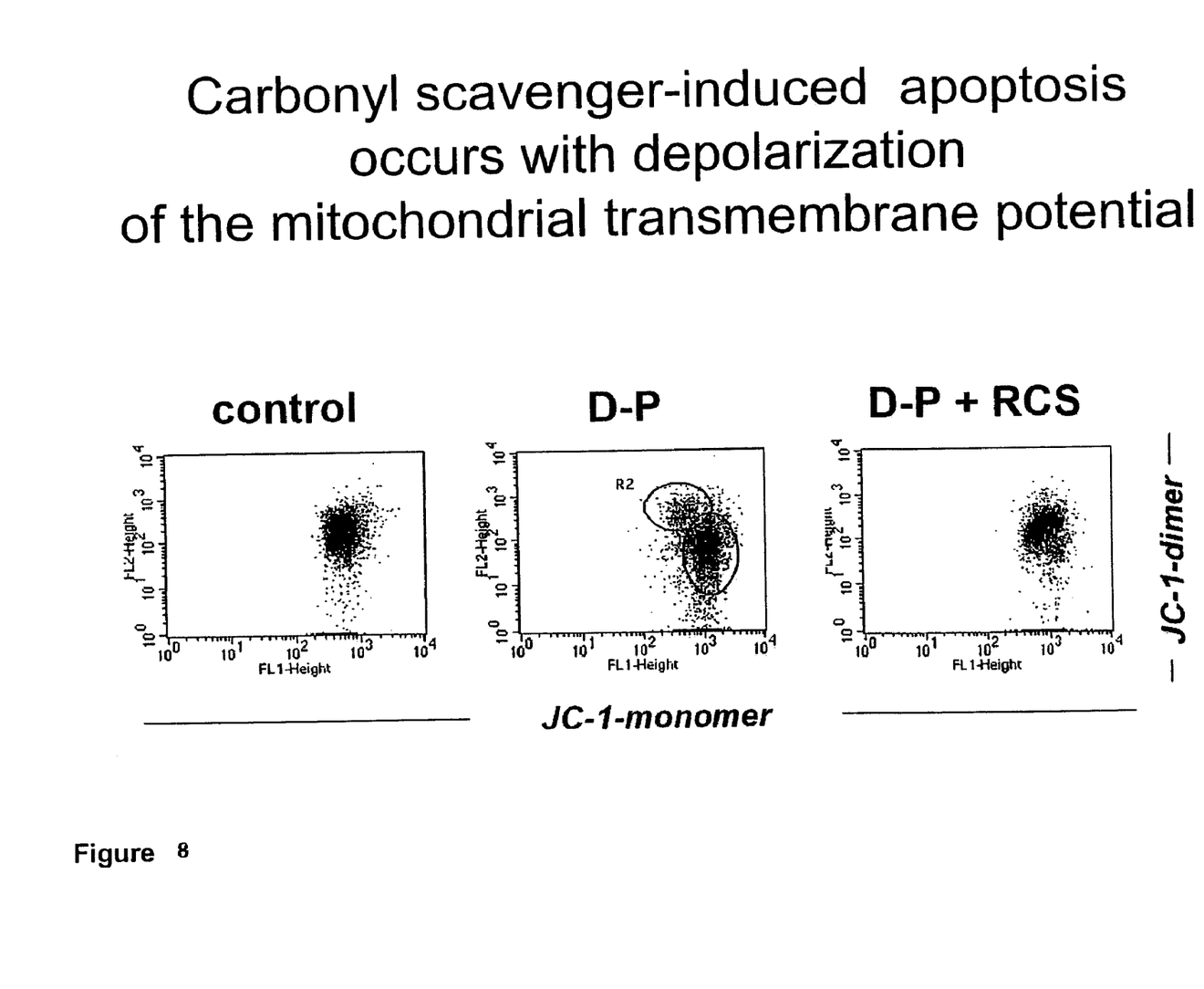
FIG. 8 shows that the apoptotic mechanism involves depolarization of the mitochondrial transmembrane potential.

FIG. 8 indicates, quite clearly, that mitochondrial transmembrane potential was lost, when cells were treated with the carbonyl scavenger and that mitochondrial transmembrane potential was preserved when cells were pretreated with phenylglyoxal and then treated with the carbonyl scavenger.

The foregoing disclosure sets forth features of the invention, which are methods for inducing cell death via the administration to a subject of a carbonyl scavenger, in an amount and in a manner sufficient to induce death of the cells to which the scavenger is administered.

In practice, the carbonyl scavenger is administered to a subject for whom the enhancement of cell death is desirable. Non-cancerous, precancerous and cancerous hyperproliferative cell disorders are encompassed by the invention, as are conditions where an inappropriate and/or abnormal increase in cells are seen, examples being inflammatory hyperproliferative states, benign prostate hyperplasia, Barrett's esophagus, virally induced plantar and genital warts, actinic keratosis, nonmelanoma and melanoma skin cancer. The evidence presented supra shows that the scavengers only function as cell death inducers in abnormal cells. Hence, there is no issue as to provoking premature or inappropriate death of normal cells.

The carbonyl scavenger used may be any of those discussed and exemplified supra. Other carbonyl scavengers may be identified and used. U.S. Pat. No. 6,716,635, supra, incorporated by reference, teaches how to identify such compounds.

Modes of administration can vary. Topical administration in, e.g., the form of a lotion, créme, wash, roll-on, soap, etc., is one preferred form of administration, but intradermal, subdermal, intramuscular, intravenous, oral, sublingual, etc. The form of delivery will vary, depending upon the condition being treated.

Other aspects of the invention will be clear to the skilled artisan, and need not be reiterated here.

The terms and expression which have been employed are used as terms of description and not of limitation, and there is no intention in the use of such terms and expression of excluding any equivalents of the features shown and described or portions thereof, it being recognized that various modifications are possible with the scope of the invention.

We claim:

1. A method for inducing or accelerating cell death in an abnormal cell, wherein the abnormal cell is a melanoma, a squamous carcinoma cell, an adenocarcinoma cell, an epithelial carcinoma cell, or a premalignant keratinocyte, comprising administering to said abnormal cell an amount of a carbonyl scavenger sufficient to induce or to accelerate death of said abnormal cell, wherein said carbonyl scavenger is D-penicillamine, amino guanidine, or 3 methyl-3 ethyl cysteine(MEC).

2. The method of claim 1, comprising administering said carbonyl scavenger topically.

3. The method of claim 1, further comprising administering said carbonyl scavenger to a human being.

4. The method of claim 1, wherein said abnormal cell is a melanoma cell.

5. The method of claim 1, wherein said abnormal cell is a squamous cell carcinoma cell.

6. The method of claim 1, wherein said abnormal cell is an epithelial carcinoma cell.

7. The method of claim 1, wherein said abnormal cell is an adenocarcinoma cell.

8. The method of claim 1, wherein said carbonyl scavenger is penicillamine.

9. The method of claim 1, wherein said carbonyl scavenger is amino guanidine.

10. The method of claim 1, wherein said carbonyl scavenger is 3 methyl-3 ethyl cystien (MEC) methyl, ethyl cysteine.

* * * * *